US010264975B2

(12) United States Patent
Tamura et al.

(10) Patent No.: US 10,264,975 B2
(45) Date of Patent: Apr. 23, 2019

(54) SUBJECT OBSERVATION SYSTEM AND METHOD, AND CAPSULE-TYPE ENDOSCOPE SYSTEM

(71) Applicant: OLYMPUS CORPORATION, Tokyo (JP)

(72) Inventors: Kazuaki Tamura, Hachioji (JP); Takeshi Ito, Hino (JP); Iwao Komazaki, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 130 days.

(21) Appl. No.: 14/752,188

(22) Filed: Jun. 26, 2015

(65) Prior Publication Data

US 2015/0289764 A1 Oct. 15, 2015

Related U.S. Application Data

(63) Continuation of application No. PCT/JP2013/084667, filed on Dec. 25, 2013.

(30) Foreign Application Priority Data

Dec. 27, 2012 (JP) ................................ 2012-285556

(51) Int. Cl.
*A61B 5/00* (2006.01)
*A61B 1/04* (2006.01)
(Continued)

(52) U.S. Cl.
CPC ............ *A61B 5/0071* (2013.01); *A61B 1/041* (2013.01); *A61B 1/0638* (2013.01);
(Continued)

(58) Field of Classification Search
CPC ................................................... A61B 5/0071
See application file for complete search history.

(56) References Cited

U.S. PATENT DOCUMENTS

2011/0237894 A1 9/2011 Ozawa et al.
2011/0273548 A1 11/2011 Uchiyama et al.
(Continued)

FOREIGN PATENT DOCUMENTS

CN 102204809 A 10/2011
CN 102309307 A 1/2012
(Continued)

OTHER PUBLICATIONS

English translation of International Preliminary Report on Patentability dated Jul. 9, 2015 together with the Written Opinion received in related International Application No. PCT/JP2013/084667.

(Continued)

*Primary Examiner* — Michael W Kahelin
(74) *Attorney, Agent, or Firm* — Scully, Scott, Murphy & Presser, P.C.

(57) ABSTRACT

A subject observation system includes a light source and an image obtaining unit. The light source emits observation light including a spectral component of a wavelength and applies the light to a subject. The image obtaining unit images reflected light from an irradiation region of the subject to which the light has been applied and obtains at least two observation images in different wavelength regions based on image signals corresponding to a blue region, a green region and a red region. The light includes components of light emission spectra in the regions. The light emission spectrum in the blue region is smaller in a wavelength region in which absorption intensity for a specific observation target in the subject is relatively low than in other regions.

22 Claims, 7 Drawing Sheets

(51) Int. Cl.
*A61B 1/06* (2006.01)
*A61B 5/07* (2006.01)

(52) U.S. Cl.
CPC .......... *A61B 1/0653* (2013.01); *A61B 5/0084* (2013.01); *A61B 5/073* (2013.01)

(56) References Cited

U.S. PATENT DOCUMENTS

| | | |
|---|---|---|
| 2011/0288387 A1 | 11/2011 | Machida et al. |
| 2012/0010465 A1 | 1/2012 | Erikawa et al. |
| 2012/0197076 A1 | 8/2012 | Minetoma |

FOREIGN PATENT DOCUMENTS

| | | |
|---|---|---|
| CN | 102613953 A | 8/2012 |
| EP | 2 404 544 A1 | 1/2012 |
| JP | 2005205195 A2 | 8/2005 |
| JP | 2012016545 A2 | 1/2012 |
| JP | 2012-143397 A | 8/2012 |
| JP | 2012-152459 A | 8/2012 |
| JP | 2012228443 A2 | 11/2012 |

OTHER PUBLICATIONS

Extended Supplementary European Search Report dated Jul. 15, 2016 in related European Application No. 13 86 9001.1.
Chinese Office Action dated Nov. 1, 2016 in corresponding Chinese Patent Application No. 201380068349.2.
Japanese Office Action dated Nov. 8, 2016 in corresponding Japanese Patent Application No. 2012-285556.
International Search Report dated Feb. 10, 2014 issued in PCT/JP2013/084667.
Chinese Office Action dated Mar. 11, 2016 in related Chinese Patent Application No. 201380068349.2.
Chinese Office Action dated May 5, 2017 in Chinese Patent Application No. 201380068349.2.
Japanese Office Action dated Mar. 28, 2017 in Japanese Patent Application No. 2012-285556.
European Patent Office Communication dated Mar. 2, 2018 in corresponding European Patent Application No. 13 869 001.1.
Chinese Office Action dated Sep. 30, 2017 in Chinese Patent Application No. 201380068349.2.

Absorption/fluorescence characteristics of first fluorescent substance (yellow)

Spectral sensitivity characteristic of imaging element

Spectral intensity characteristic of observation light

Absorption characteristic of living tissue

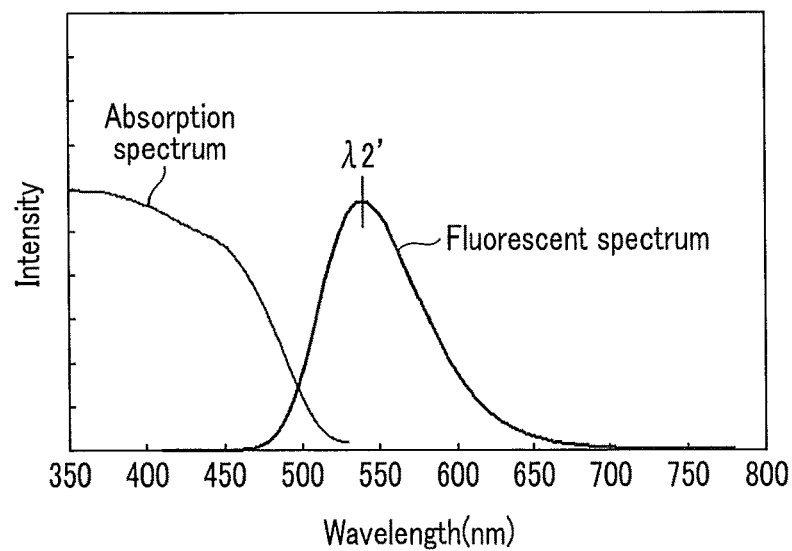
Absorption/fluorescence characteristics of first fluorescent substance (green)
F I G. 8
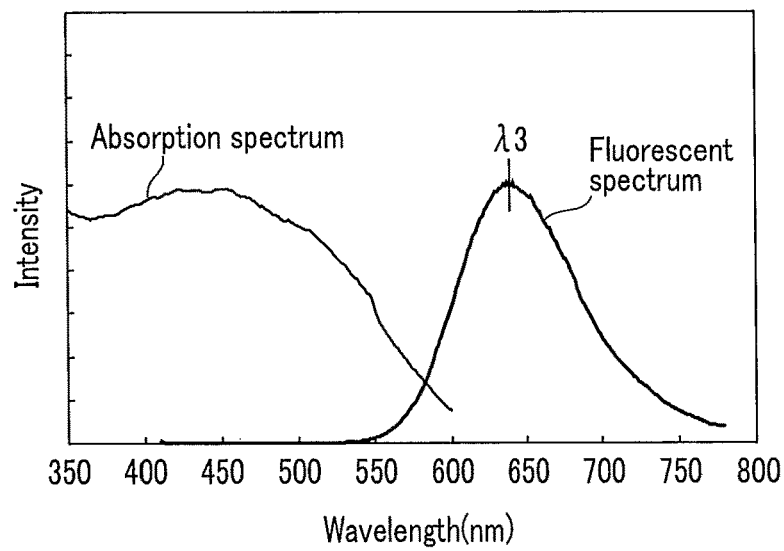
Absorption/fluorescence characteristics of second fluorescent substance (red)
F I G. 9

Spectral intensity characteristic of observation light

SUBJECT OBSERVATION SYSTEM AND METHOD, AND CAPSULE-TYPE ENDOSCOPE SYSTEM

CROSS-REFERENCE TO RELATED APPLICATIONS

This is a Continuation Application of PCT Application No. PCT/JP2013/084667, filed Dec. 25, 2013, which was published under PCT Article 21(2) in Japanese.

This application is based upon and claims the benefit of priority from prior the Japanese Patent Application No. 2012-285556, filed Dec. 27, 2012; the entire contents of which are incorporated herein by references.

BACKGROUND OF THE INVENTION

1. Field of the Invention

The present invention relates to a subject observation system and a method thereof, and a capsule-type endoscope system to perform observations such as a normal observation by white light and an observation by light having a wavelength different from a wavelength in the normal observation, for example, by special light for observing a particular subject.

2. Description of the Related Art

For example, a subject observation system such as an endoscope comprises a light emitting apparatus to apply white light and the like to a subject. One such light emitting apparatus has been currently developed, wherein a wavelength converting member is disposed at the distal end of an optical fiber, and light output from a small solid state light source is wavelength-converted by the wavelength converting member, whereby the light is changed to a desired irradiation pattern and/or color. Jpn. Pat. Appln. KOKAI Publication No. 2005-205195 discloses a light emitting apparatus and an endoscope apparatus using the same which can emit various colors by a combination of an excitation light source and wavelength converting members disposed at the distal end of an optical fiber.

BRIEF SUMMARY OF THE INVENTION

According to an embodiment of the present invention, there is provided a subject observation system comprising a subject observation light source configured to emit observation light including a spectral component of a predetermined wavelength and apply the observation light to a subject and an image obtaining unit configured to image reflected light from an irradiation region of the subject to which the observation light has been applied, and obtain at least two observation images in different wavelength regions on the basis of a plurality of image signals corresponding to a blue region, a green region and a red region, respectively, wherein the observation light includes components of light emission spectra in the blue region, the green region and the red region, and the light emission spectrum in the blue region is smaller in a wavelength region in which absorption intensity for a specific observation target in the subject is relatively low than in other regions.

According to another embodiment of the present invention, there is provided a subject observation method comprising using a subject observation light source to generate observation light including a spectral component of a predetermined wavelength by light emission and apply the observation light to a subject; using an imaging section to image reflected light from an irradiation region of the subject to which the observation light has been applied, and obtaining at least two observation images in different wavelength regions on the basis of image signals corresponding to a blue region, a green region and a red region output from the imaging section, wherein the observation light includes components of light emission spectra in the blue region, the green region and the red region, and the light emission spectrum in the blue region is smaller in a wavelength region in which absorption intensity for a specific observation target in the subject is relatively low than in other regions.

According to a further embodiment of the invention, there is provided a capsule-type endoscope system being provided with the above subject observation system.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 8 is a graph showing absorption/fluorescence characteristics of a first fluorescent substance in the modification of the wavelength converting unit;

FIG. 9 is a graph showing absorption/fluorescence characteristics of a second fluorescent substance in the modification of the wavelength converting unit;

DETAILED DESCRIPTION OF THE INVENTION

[First Embodiment]

Hereinafter, a first embodiment according to the present invention will be described with reference to the drawings.

In describing the present embodiment, the relation between a color region and a wavelength region in the embodiment is defined as below. A blue region has a wavelength region of 380 nm to 500 nm, a green region has a wavelength region of 500 nm to 600 nm, and a red region has a wavelength region of 600 nm to 720 nm. The wavelength regions in which the sensitivities of blue pixels, green pixels and red pixels of an imaging section are maximized in the present embodiment are the blue region, the green region and the red region, respectively.

A subject Q is, for example, a human body, and is a living tissue J including a blood vessel K. Blood flows through the blood vessel K, and hemoglobin is contained in the blood.

Figure 1:
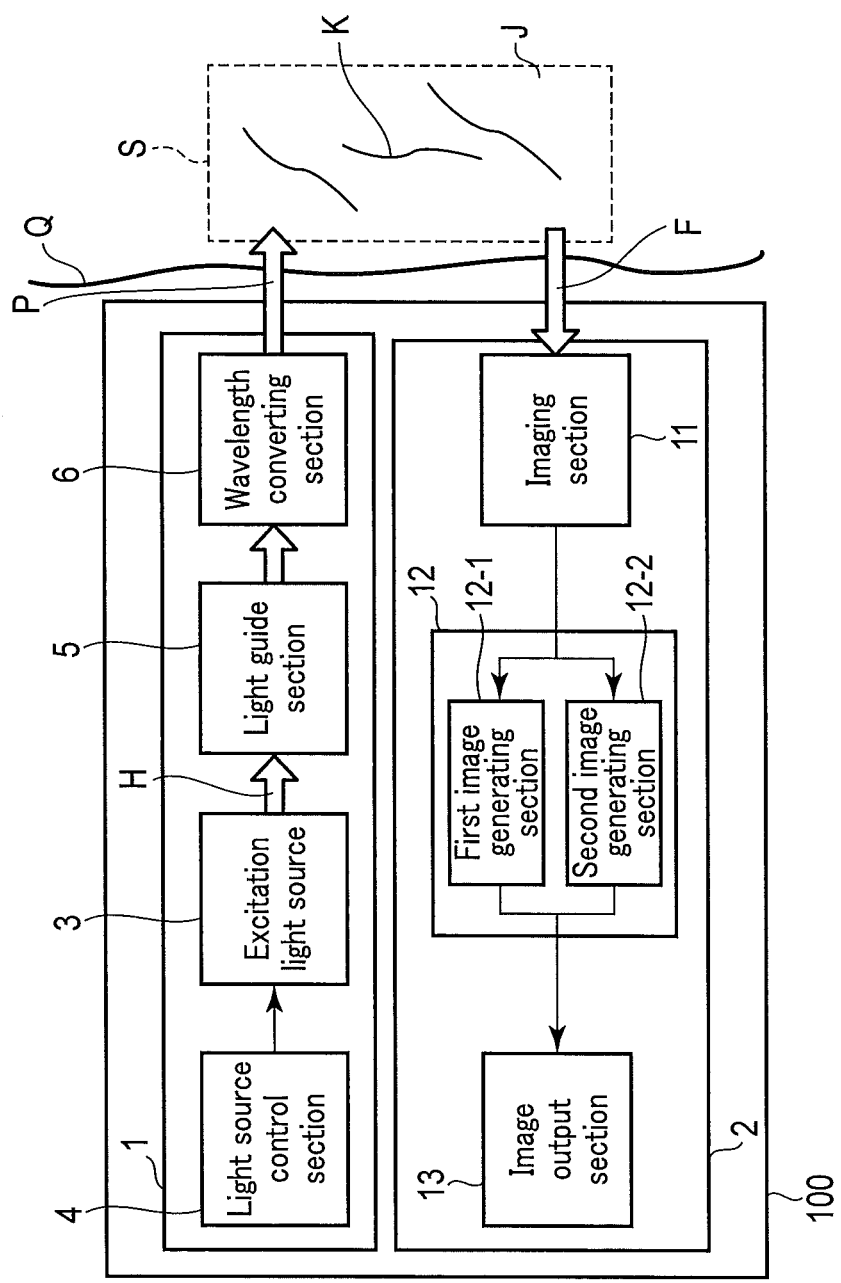
FIG. 1 is a block diagram showing a first embodiment of a subject observation system according to the present invention.

FIG. 1 shows a block diagram of a subject observation system 100. The subject observation system 100 comprises a subject observation light source 1 which applies observation light P to the subject Q such as a human body, and an image obtaining unit 2 for obtaining image information about the subject Q.

The subject observation light source 1 emits the observation light P including a spectral component of a predetermined wavelength, and applies the observation light P to the subject Q. The subject observation light source 1 comprises an excitation light source 3, a light source control section 4, a light guide section 5, and a wavelength converting section 6.

The excitation light source 3 emits excitation light H which is a first light emission spectral component having the wavelength of a light emission peak in a wavelength region of 400 nm to 440 nm (or 400 nm to 415 nm) included in the blue region.

The light source control section 4 drives and controls the excitation light source 3.

The light guide section 5 guides the excitation light H emitted from the excitation light source 3 to the wavelength converting section 6.

The wavelength converting section 6 absorbs part of the excitation light H and converts it to wavelength-converted light in a wavelength region closer to a long-wavelength side than the excitation light H, and emits observation light P which is mixed light of the excitation light H and the wavelength-converted light.

Figure 2:
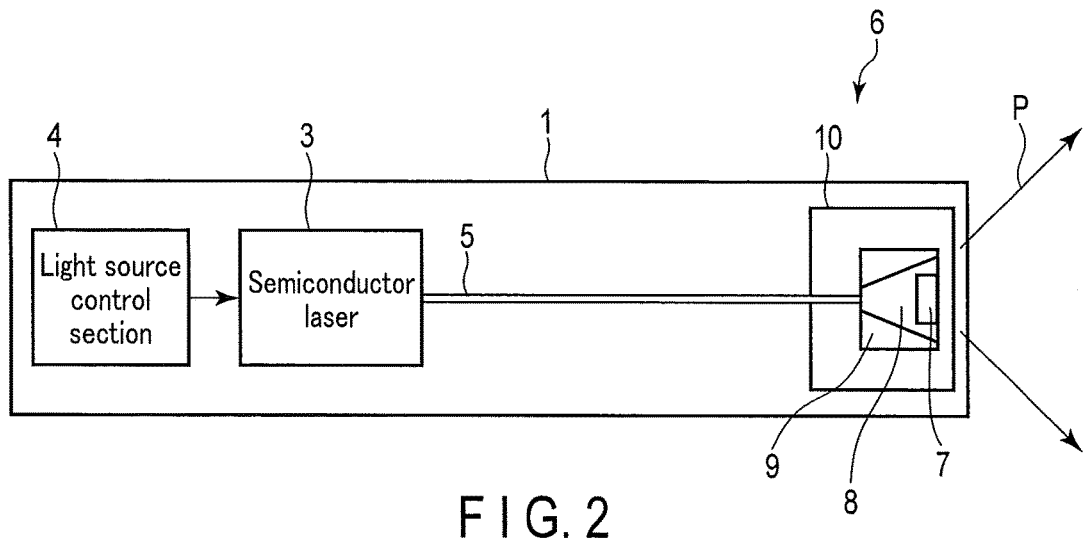
FIG. 2 is a specific diagram showing a subject observation light source in the system.

FIG. 2 shows a specific diagram of the subject observation light source 1. The excitation light source 3 is, for example, a semiconductor laser to emit the excitation light H which is the first spectral component, specifically a laser diode (LD). The excitation light source 3 emits a first light emission spectrum including the wavelength of a light emission peak in a wavelength region of 400 nm to 440 nm (or 400 nm to 415 nm) included in the blue region as described above. Specifically, the semiconductor laser 3 emits the excitation light H in the blue region having a light emission peak at a wavelength of 420 nm ($\lambda 1$) and having a half-value width at a wavelength of several nm or less, that is, blue laser light which is the first spectral component.

The light source control section 4 drives and controls the semiconductor laser 3 to emit the excitation light H from the semiconductor laser 3. The light source control section 4 controls a driving electric current and a driving method such as pulse driving and continuous driving (CW) of the semiconductor laser 3.

The light guide section 5 guides the excitation light H emitted from the excitation light source 3 to the wavelength converting section 6. The light guide section 5 is, for example, an optical fiber. The optical fiber 5 is, for example, a multimode optical fiber having a core diameter of 50 µm and a numerical aperture FNA=0.2. A coupling lens (not shown) is provided between the semiconductor laser 3 and the optical fiber 5, which converges the excitation light H emitted from the semiconductor laser 3 and couples the excitation light H to the optical fiber 5.

The wavelength converting section 6 transmits part of the excitation light H in the blue region emitted from the excitation light source 3, and also absorbs part of the excitation light H in the blue region. The absorbed excitation light is wavelength-converted to light in a wavelength region closer to the long-wavelength side than the excitation light H, for example, light in a yellow region. The wavelength converting section 6 then emits the observation light P which is the mixed light of the transmitted excitation light H and the wavelength-converted light. The wavelength converting section 6 is disposed on the emission end side of the optical fiber 5. The wavelength converting section 6 comprises a wavelength converting unit 10 in which a first fluorescent substance 7 as a wavelength converting member, a light transmitting member 8, and a holder 9 are integrally formed.

The observation light P includes components of light emission spectra in the blue region, the green region and the red region. The light emission spectrum in the blue region is small in a wavelength region in which light having absorption intensity for a specific observation target such as hemoglobin is relatively difficult to absorb.

The peak wavelength of the light emission spectrum in the blue region exists in a wavelength region having an absorption coefficient equal to or more than one fifth of the value of the absorption coefficient of the absorption peak wavelength at which the absorption coefficient of a specific observation target such as hemoglobin in a visible light range is maximized.

The maximum intensity of the light emission spectrum in the blue region is higher than the maximum intensities of the light emission spectra in the green region and the red region.

The peak wavelength of the light emission spectrum in the green region exists in a wavelength region having an absorption coefficient equal to or more than half of the value of the absorption coefficient at the absorption peak wavelength at which the absorption coefficient of a specific observation target such as hemoglobin in a wavelength region of 525 nm to 555 nm included in the green region is maximized.

Specifically, the wavelength converting section 6 absorbs part of the blue laser light (first light emission spectrum) emitted from the semiconductor laser 3. The wavelength converting section 6 also wavelength-converts the blue laser light to fluorescence (second light emission spectrum) in the broad yellow region including a wavelength region of 525 nm to 555 nm included in the green region, and then emits the observation light P which consists of the superposition of the first light emission spectrum and the second light emission spectrum. The component ratio between the first light emission spectrum and the second light emission spectrum is set so that the wavelength converting section 6 mixes the first light emission spectrum and the second light emission spectrum at a predetermined ratio and emits substantially white light as the observation light P.

The first fluorescent substance 7 includes a Eu (europium)-activated silicate-based fluorescent material (hereinafter referred to as a silicate fluorescent material). The silicate fluorescent material absorbs blue laser light having a wavelength of 420 nm emitted by the semiconductor laser 3 and then emits yellow fluorescence (hereinafter referred to as yellow fluorescence). Specifically, the silicate fluorescent material absorbs the first light emission spectrum of the excitation light H (the blue laser light which is the first spectral component) emitted from, for example, the laser diode which is the excitation light source 3, and emits the second light emission spectrum (yellow fluorescence) including a peak wavelength at a wavelength of 525 nm or more.

Figure 3:
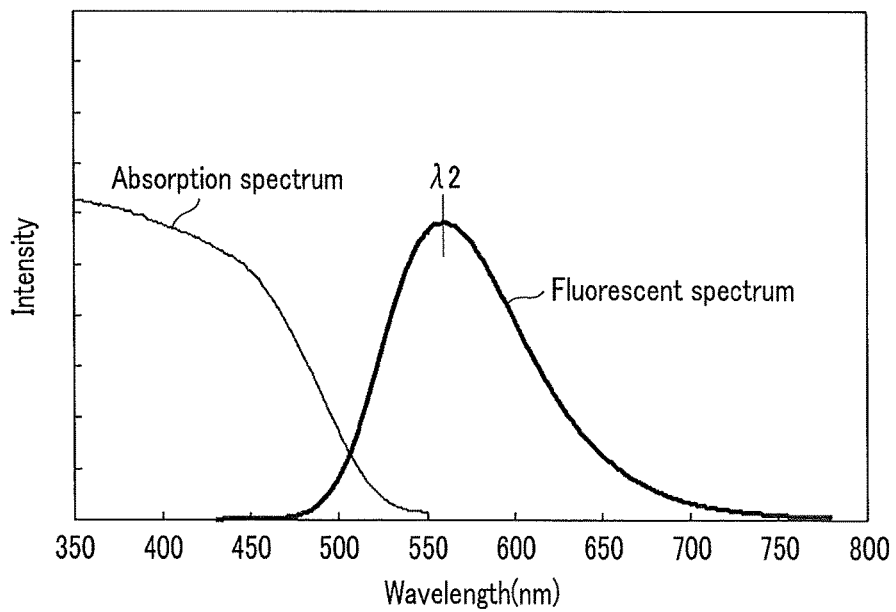
FIG. 3 is a graph showing absorption/fluorescence characteristics of a wavelength converting member (first fluorescent substance) in the system.

The first fluorescent substance 7 generally has the following optical characteristics. FIG. 3 shows absorption/fluorescence spectral characteristics of the first fluorescent substance 7. If a region in which the absorption intensity is half the peak value or more is defined as an absorption region of an absorption spectrum, the absorption region of the first fluorescent substance 7 in a visible light range having a wavelength of 380 nm to 780 nm is about a wavelength of 380 nm to 480 nm.

A fluorescent spectrum has a fluorescent peak existing at a wavelength of 565 nm ($\lambda 2$), and its half-value width includes a broad fluorescent spectrum (second light emission spectrum) having a wavelength of 95 nm. The waveform of the fluorescent spectrum includes characteristics having a gradual inclination on the long-wavelength side than on the short-wavelength side relative to a fluorescent peak wavelength. The short-wavelength end of the fluorescent half-value width is at a wavelength of 521 nm ($\lambda 2-44$ nm), and the long-wavelength end of the fluorescent half-value width is at a wavelength of 616 nm ($\lambda 2+51$ nm).

The fluorescence (second light emission spectrum) in the yellow region emitted from the first fluorescent substance 7 includes a continuous light emission spectral component in a wavelength region of 525 nm to 600 nm included in the green region to the red region. The minimum intensity of the wavelength region of 525 nm to 600 nm of the fluorescence (second light emission spectrum) in the yellow region is equal to or more than one fifth of the peak intensity of the second light emission spectrum.

The first fluorescent substance 7 is formed by dispersing a powdered silicate fluorescent material into a sealing material such as a silicone resin or glass and then solidifying the sealing material. The thickness of the fluorescent substance 7 and the concentration conditions of the silicate fluorescent material mixed into the sealing material are set to predetermined conditions to transform part of the blue laser light into desired fluorescence, for example, into yellow fluorescence in consideration of, for example, the degree of the excitation light absorption coefficient and the degree of wavelength conversion efficiency of the silicate fluorescent material.

The light transmitting member 8 is made of glass having a high transmittance or a silicone resin. The light transmitting member 8 has the properties of transmitting the excitation light H emitted from the emission end of the optical fiber 5 and the wavelength-converted light (yellow fluorescence) emitted from the first fluorescent substance 7.

The holder 9 holds the light transmitting member 8 and the first fluorescent substance 7. The holder 9 includes an entrance portion through which the excitation light H enters, and an exit portion which emits part of the excitation light H and the yellow fluorescence. The holder 9 is tapered at the inside thereof. A reflective member is formed on the inner circumferential surface of the tapered shape, which regularly reflects or diffusely reflects the excitation light H and the yellow fluorescence. The first fluorescent substance 7 is located on the optical path axis of the excitation light H which enters from the entrance portion of the holder 9.

On the other hand, the image obtaining unit 2 images reflected light F from an irradiation region S of the subject Q to which the observation light P has been applied, and obtains at least two observation images of the subject in different wavelength regions on the basis of image signals corresponding to the blue region, the green region and the red region, such as a normal light observation image and a special light observation image. The image obtaining unit 2 comprises an imaging section 11, an image processing section 12, and an image output section 13. The image processing section 12 includes a first image generating section 12-1 and a second image generating section 12-2.

The imaging section 11 images the reflected light F from the region (irradiation region) S of the subject Q which has been irradiated by the subject observation light source 1. The imaging section 11 includes, for example, a solid state image sensor (CCD). The CCD includes blue pixels (B pixels), green pixels (G pixels) and red pixels (R pixels). The CCD transmits pixel signals output from the BGR pixels to the image processing section 12.

Figure 4:
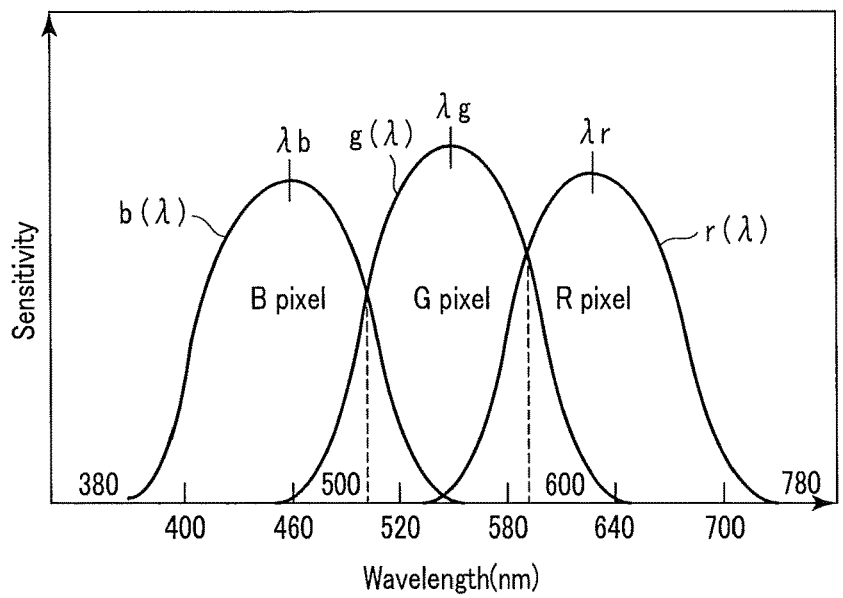
FIG. 4 is a graph showing sensitivity characteristics of a general CCD in an imaging section in the system.

FIG. 4 shows sensitivity characteristics of a general CCD. Specifically, the CCD includes the B pixels having a sensitivity peak at a wavelength of 460 nm ($\lambda b$) in the blue region, the G pixels having a sensitivity peak at a wavelength of 540 nm ($\lambda g$) in the green region, and the R pixels having a sensitivity peak at a wavelength of 630 nm ($\lambda r$) in the red region. The excitation light H (blue laser light) which is the first spectral component exists in the blue region.

The sensitivity region of the B pixels exists up to a wavelength of 540 nm on the long-wavelength side, and the sensitivity region of the R pixels exists up to a wavelength of 540 nm on the short-wavelength side. Therefore, the B pixels and the G pixels, and the G pixels and the R pixels respectively include wavelength regions having overlapping sensitivities in adjacent wavelength regions.

Here, the light receiving sensitivity characteristic of the B pixels to a wavelength $\lambda$ is defined as $b(\lambda)$, the light receiving sensitivity characteristic of the G pixels is defined as $g(\lambda)$, and the light receiving sensitivity characteristic of the R pixels is defined as $r(\lambda)$.

Pixel signals of the B pixels, the G pixels and the R pixels output from the CCD of the imaging section 11 are input to the image processing section 12. From the pixel signals, the first image generating section 12-1 generates a normal light observation image as a first image of the subject Q, and the second image generating section 12-2 generates a special light observation image as a second image.

Specifically, the first image generating section 12-1 generates a normal light observation image of the subject Q on the basis of the pixel signals corresponding to the blue region, the green region and the red region that are obtained when the reflected light F is imaged by the imaging section 11. That is, the first image generating section 12-1 generates the normal light observation image on the basis of the levels of the pixel signals of the B pixels, the G pixels and the R pixels output from the CCD of the imaging section 11.

The second image generating section 12-2 generates a special light observation image that enhances a special observation target in the subject Q, for example, hemoglobin flowing through the blood vessel K on the basis of the levels of the pixel signals of B pixels and G pixels among the B pixels, the G pixels and the R pixels output from the CCD.

The first image generating section 12-1 and the second image generating section 12-2 also include functions of generating images in parallel in one frame period, and generating two images: the normal light observation image and the special light observation image. Specifically, the first image generating section 12-1 and the second image generating section 12-2 respectively obtain the normal light observation image and the special light observation image of the same part of the subject Q on the basis of the image signals for one frame obtained by the B pixels, the G pixels and the R pixels of the imaging section 11.

The image processing section 12 holds a white balance coefficient that determines color information at the time of the normal light observation image and the special light observation image. The white balance coefficient is set by using a white plate having a substantially flat reflection characteristic in the visible light range for the sensitivity characteristic resulting from multiplication of, for example, P(λ) which is a light emission intensity characteristic relative to the wavelength λ of the observation light P, and b(λ), g(λ) and r(λ) which are the light receiving sensitivity characteristics of the CCD of the imaging section 11.

Each of the color components B, G and R of blue, green and red provided by multiplying the P(λ) of the observation light P by b(λ), g(λ) and r(λ) of the CCD of the imaging section 11 respectively are calculated as below.

$$B = \int_{380}^{780} P(\lambda) \cdot b(\lambda) d\lambda$$

$$G = \int_{380}^{780} P(\lambda) \cdot g(\lambda) d\lambda$$

$$R = \int_{380}^{780} P(\lambda) \cdot r(\lambda) d\lambda \quad \text{[Expression 1]}$$

For example, when the reflection characteristic (absorption characteristic) of the white plate is constant in the visible light range, B/G is a white balance coefficient Wb of B to G, and R/G is a white balance coefficient Wr of R to G.

In the case where the white balance coefficients Wb and Wr of the color components B and R are 1.0, the balance of the color components B, G and R is satisfactory when the spectral characteristic of the observation light P and the sensitivity characteristics of the pixels of the CCD are multiplied.

As a result of the correction by the white balance coefficients Wb and Wr, it is possible to generate the normal light observation image and the special light observation image even if the spectrum of the observation light P is different from that of the white light.

Noise of some pixels is amplified at the time of color balance setting and noise of the generated image increases if the numerical values of the white balance coefficients Wb and Wr are extremely low or high, so that the white balance coefficients Wb and Wr preferably range from ⅓ to 3.

Therefore, regarding a color component ratio in the observation light P, the intensity of red light having a wavelength of 600 nm or more at which the R pixels included in the red region includes the maximum intensity is preferably equal to or more than one third of the intensity of green light in the wavelength region in which the green pixels include the maximum intensity, for example, at a wavelength of 525 nm to 555 nm.

The image output section 13 outputs the normal light observation image and the special light observation image generated in the image processing section 12 to, for example, a CRT display or liquid crystal display not shown. The image output section 13 may include a storage section to store the images in, for example, a memory card or a hard disk and the like.

Next, the operation of the system having the above configuration is described.

The operation for emitting the observation light P from the subject observation light source 1 is as follows.

To observe the subject Q by the subject observation system 100, the light source control section 4 turns on the semiconductor laser as the excitation light source 3 on the basis of input setting information from the exterior. The semiconductor laser 3 is then turned on, the semiconductor laser 3 emits blue laser light having a wavelength of 420 nm.

The blue laser light emitted from the semiconductor laser 3 enters the optical fiber 5 and is then guided by the optical fiber 5, and enters the wavelength converting unit 10 located at the emission end of the optical fiber 5.

The blue laser light having a wavelength of 420 nm includes the wavelength of the absorption region of the silicate fluorescent material included in the first fluorescent substance 7. Part of the blue laser light which has entered the wavelength converting unit 10 is wavelength-converted by the first fluorescent substance 7 to yellow fluorescence of a broad spectrum having a peak around a wavelength of 565 nm.

Mixed light of the blue laser light having a wavelength of 420 nm which has entered the wavelength converting unit 10 and has not been absorbed in the first fluorescent substance 7 and the yellow fluorescence having a peak around a wavelength of 565 nm which has been wavelength-converted by the first fluorescent substance 7 is emitted as the observation light P from the emission end of the wavelength converting unit 10 as shown in FIG. 2.

Figure 5:
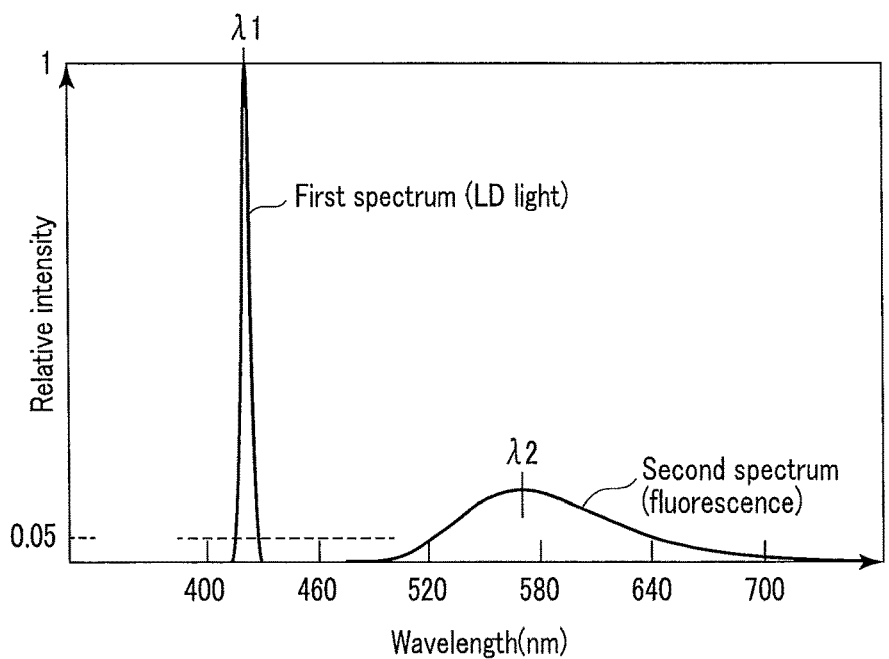
FIG. 5 is a graph showing the spectral characteristic of observation light emitted from the subject observation light source in the system.

FIG. 5 shows the spectral characteristic P(λ) of the observation light P. Including a spectral component in the region of each wavelength (the region of each color) is defined as a region having an intensity higher than 1/20 of the maximum intensity of each color region, and a region with an intensity less than or equal to 1/20 of the maximum intensity does not include any spectral component.

The observation light (mixed light) P mainly includes the narrow-band blue laser light (first spectral component) having a peak at a wavelength of 420 nm, and the yellow fluorescence (second spectral component) having a peak around a wavelength of 565 nm. The observation light (mixed light) P is set to a component ratio around the white light between the blue laser light and the yellow fluorescence.

The maximum intensity of a wavelength of 450 nm to 480 nm between the blue laser light and the yellow fluorescence in the observation light P is less than or equal to 1/20 of the intensity of the peak wavelength (λ1) of the blue laser light. The light intensity at a wavelength of 450 nm to 480 nm in the observation light P is less than or equal to 1/20 of the light intensity at a wavelength of 400 nm to 440 nm.

The light intensity ratio between the blue region, the green region and the red region of the observation light P is, for example, about 5 (blue), 3 (green) and 2 (red). The wavelength difference between the peak wavelength λ1 of the blue laser light and the peak wavelength λ2 of the fluorescence is about 150 nm. The wavelength difference between the half-value width end of the blue laser light and the half-value width end of the yellow fluorescence is about 80 nm.

The observation light P emitted from the wavelength converting unit 10 has a predetermined light distribution angle. For the observation light P, the irradiation region S to irradiate the subject Q shown in FIG. 1 is formed in accordance with the light distribution angle and the distance between the emission end of the wavelength converting unit 10 and the subject Q.

Next, the operation when the observation light P is applied to the subject Q is described.

In the subject Q, there are at least two kinds of tissues different in absorption characteristic: the blood vessel K and the living tissue J (e.g., mucous membrane) as shown in FIG. 1.

Figure 6:
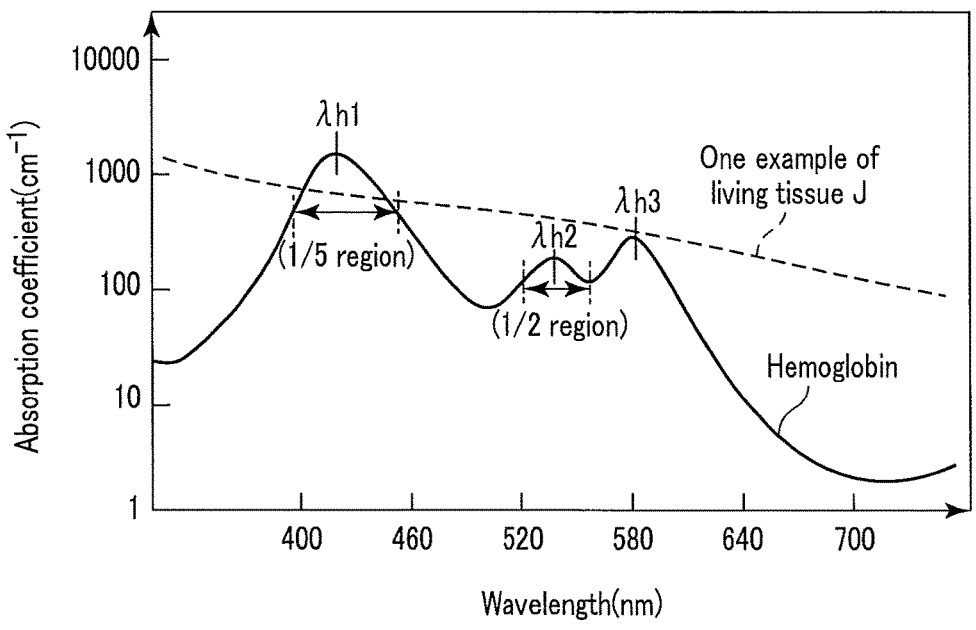
FIG. 6 is a graph showing an absorption coefficient which serves as an index of the absorption intensity of hemoglobin in a blood vessel in a subject to be observed by the system.

FIG. 6 shows an absorption coefficient which serves as an index of the absorption intensity of hemoglobin in the blood vessel K in the subject Q. In the visible light range at a wavelength of 380 nm to 780 nm, hemoglobin has absorption intensity peaks at different wavelengths: around a wavelength of 415 nm (λh1), around a wavelength of 540 nm (λh2) and around a wavelength of 580 nm (λh3), and has the properties of having the highest absorption intensity around the wavelength of 415 nm (λh1).

In general, an NBI (Narrow Band Imaging) observation of an endoscope uses, as observation light, light at two wavelengths including wavelength regions around a wavelength of 415 nm (λh1) and around a wavelength of 540 nm (λh2): light at a wavelength of about 400 nm to 440 nm and light in a wavelength region of about 525 nm to 555 nm.

Furthermore, in the NBI observation, there has been known a technique (special light observation) that facilitates the discovery of, for example, carcinomata and the like by observing the blood vessel K with high contrast using the fact that the lights at the two wavelengths have the properties of having different light depths upon entering the living tissue J from the surface and scattering characteristics.

The observation light P according to the present embodiment includes a component to be white light by the blue laser light at a wavelength of 420 nm and the yellow fluorescence having a peak around a wavelength of 565 nm.

The blue laser light at a wavelength of 420 nm is absorbed and scattered in the relatively superficial part of the living tissue J, and is therefore advantageous to the observation of the blood vessel K in the vicinity of the surface of the living tissue J.

On the other hand, the yellow fluorescence includes light of a broad spectrum around a wavelength of 540 nm (λh2). The light around a wavelength of 540 nm is scattered to some degree when applied to the living tissue J but travels deeper into the skin than the light at a wavelength of 420 nm. Thus, the light around a wavelength of 540 nm is absorbed and scattered in, for example, the blood vessel K under the skin, and is therefore advantageous to the observation of the blood vessel K of a subcutaneous tissue. Preferably, the peak wavelength λ2 of the fluorescent component exists in the wavelength band of the absorption coefficient equal to or more than half of the absorption coefficient of an absorption peak wavelength of 540 nm (λh2) of hemoglobin in the green region so that the ratio of absorption at the observation of the blood vessel K of the subcutaneous tissue increases, and the sensitivity of the green pixels increase. Consequently, a high contrast image can be obtained at the peak wavelength λ2 of the fluorescent component.

In contrast, the absorption characteristic of hemoglobin shows that its absorption intensity tends to sharply decrease from a wavelength of around 415 nm (λh1) to the long-wavelength side as shown in FIG. 6. For example, when the absorption coefficient at a wavelength of 450 nm is compared to that at a wavelength of about 415 nm (λh1), the absorption characteristic of hemoglobin decreases to about ⅕ at a wavelength difference of 35 nm.

In contrast, most of the living tissues J in the subject Q show colors ranging from a flesh color to a red color. For example, as an example of the absorption characteristic of the living tissue J, the absorption coefficient gradually degreases from the blue region to the red region. The absorption coefficient of the living tissue J in the subject Q is lower than that of hemoglobin at a wavelength of around 415 nm (λh1) in the blue region. The living tissue J in the subject Q includes tissues having an absorption coefficient higher than that of hemoglobin around a wavelength of 450 nm.

To observe the blood vessel K with higher contrast, the light intensity around a wavelength of 415 nm (λh1) at which the absorption coefficient of hemoglobin is higher than that of the living tissue J is greater than the light intensity around a wavelength of 460 nm at which the absorption coefficient of hemoglobin is lower than that of the living tissue J. Thus, it is necessary to increase the ratio of the light intensity in the blue region included in the observation light P in which hemoglobin is absorbed relative to the living tissue J.

The sensitivity of the B pixels of the CCD of the imaging section 11 used to obtain images around a wavelength of 450 nm is about twice as high as the sensitivity around a wavelength of 415 nm (λh1). It is more difficult to be absorbed in the blood vessel (hemoglobin) in the vicinity of the surface of the living tissue J in a wavelength region of 450 nm to 480 nm than at a wavelength of 415 nm (λh1).

Therefore, if the light intensity in a wavelength region of 450 nm to 480 nm which is the blue region on the long-wavelength side from a wavelength of 450 nm is about half of the light intensity in a wavelength region of 400 nm to 440 nm around a wavelength of 415 nm (λh1), the light intensity in a wavelength region of 450 nm to 480 nm will have an influence as image noise when contrast is enhanced.

For the reduction of the image noise, it is advantageous to limit the light intensity in a wavelength region of 450 nm to 480 nm to less than or equal to ⅕ of the light intensity in a wavelength region of 400 nm to 440 nm. Moreover, if the light intensity is limited to 1/10 or less, it is possible to not only reduce the image noise but also obtain an image with high contrast.

The observation light P for the normal light observation is preferably white light. A continuous flat spectral component is considered to be advantageous to the observation light P over the wavelength regions ranging from the green region to the red region in order to observe colors ranging from the flesh color to the red color that are particularly largely seen in the living tissue J.

Next, the operation of receiving the reflected light F of the observation light P and generating a normal light image and a special light image is described.

Part of the observation light P is absorbed on the basis of the absorption characteristic of the blood vessel K and the living tissue J located in the irradiation region S. Part of the rest of the observation light P is scattered, reflected, and received by the CCD of the imaging section 11 having the R pixels, the G pixels and the B pixels.

Since the light receiving sensitivity characteristic of the B pixels exists in a wavelength of 380 nm to 540 nm, the reflected light F of the observation light P received by the B pixels is in the short-wavelength region of the blue laser light and the yellow fluorescence. However, the sensitivity of the B pixels is low around a wavelength of 520 nm, so that the component received in the B pixels mainly includes the blue laser light.

The light receiving sensitivity characteristic of the G pixels exists in a wavelength of 460 nm to 640 nm. It is advantageous to receive no spectral component of the blue region in the G pixels in reducing the image noise of the G pixels. To prevent the spectral component of the blue region from being received in the G pixels, it is preferable to reduce the blue component in a wavelength region of 450 nm to 480 nm included in the observation light P or separate the wavelengths of the blue component and the green component. That is, components at a wavelength of 450 nm to 480 nm include a region of 5 nm or more which is less than or equal to 1/20 of the peak intensity at a wavelength of 400 nm to 440 nm. The observation light P is set so that the wavelength region having an intensity that is less than or equal to 1/20 of the peak intensity of the first light emission spectrum continuously exists, for example, 5 nm or more in a wavelength region of 450 nm to 480 nm.

The reflected light F of the observation light P also includes a component of red region at a wavelength of 580 nm or more. The R pixels mainly receive the red fluorescent component in a sensitivity region of a wavelength region of 540 nm to 720 nm.

The imaging section 11 transfers light reception signals of the RGB pixels received by the CCD to the image processing section 12.

The first image generating section 12-1 of the image processing section 12 generates a normal light observation image on the basis of the levels of the pixel signals of the B pixels, the G pixels and the R pixels output from the CCD of the imaging section 11. That is, the first image generating section 12-1 generates the normal light observation image under observation light irradiation on the basis of the light reception signals of the B pixels, the G pixels and the R pixels, and predetermined image processing (e.g. white balance, noise reduction, structure enhancement and gamma correction). The normal light observation image is generated by using all spectral components included in the observation light P.

The second image generating section 12-2 of the image processing section 12 generates a special light observation image on the basis of the levels of the pixel signals of the B pixels and the G pixels output from the CCD of the imaging section 11. That is, the second image generating section 12-2 generates the special light observation image under observation light irradiation on the basis of signal processing that allocates the light reception signal of the B pixels as the light reception signals of the B pixels and the G pixels and allocates the light reception signal of the G pixels as the light reception signal of the R pixels, and predetermined image processing. The special light observation image is generated by only using the blue region and the green region among the components included in the observation light.

The image output section 13 outputs the normal light observation image and the special light observation image generated in the image processing section 12 to, for example, the CRT display or the liquid crystal display.

According to the operation described above, one observation light P is applied to the subject Q, and two images, one for the normal light observation and one for the special light observation for enhanced display with high contrast of the blood vessel can be obtained.

Thus, according to the first embodiment described above, the subject observation light source 1 which applies the observation light P to the subject Q, and the image obtaining unit 2 which obtains the image of the irradiation region S irradiated by the subject observation light source 1 are included. The image obtaining unit 2 obtains different observation images, for example, the normal light observation image and the special light observation image. Therefore, it is possible to obtain the subject observation system 100 that uses a small observation light source usable in both the normal light observation and the special light observation by a combination of one excitation light source 3 which emits light in a particular wavelength band and the wavelength converting section 6 in consideration of absorption characteristics of the subject Q which is an observation target.

The spectral component of the observation light P includes the blue laser light at a wavelength of 420 nm around the absorption peak of hemoglobin, and an absorption peak of 540 nm of hemoglobin in the green region. Therefore, the special light observation that only uses the blue region and the green region among the components included in the observation light can be performed together with the normal light observation. In particular, the blue light included in the observation light P is the narrow-band blue laser light, and the blue light and the green light are separated, so that it is possible to obtain an image that shows the blood vessel K in the surface of the living tissue J with high contrast. That is, the second image generating section 12-2 can generate the special light observation image under observation light irradiation on the basis of signal processing that allocates the light reception signal of the B pixels as the light reception signals of the B pixels and the G pixels and allocates the light reception signal of the G pixels as the light reception signal of the R pixels, and on the basis of predetermined image processing.

The white light also including the red light is obtained in the spectral component of the observation light P, so that the normal light observation combined with a predetermined image obtaining unit can be performed.

The spectrum of the observation light P is only composed of one excitation light source 3 and the fluorescent substance 7 as one wavelength converting member, and is therefore particularly advantageous to, for example, a transnasal endoscope in which the regions in which the excitation light source 3 and the wavelength converting unit 10 are disposed are limited.

The above-mentioned first embodiment may be modified as follows.

The excitation light source 3 may be configured so that the peak wavelength of the first light emission spectrum of the excitation light H exists in a wavelength region between the wavelength at which the absorption spectrum of the first fluorescent substance 7 in a wavelength region of 400 nm to 440 nm is maximized and the peak wavelength of the absorption of the specific observation target (hemoglobin) in the same wavelength region of 400 nm to 440 nm. That is, the blue laser light (the first light emission spectrum of the excitation light H) emitted from the semiconductor laser 3 to be used may have a peak wavelength in a wavelength of 400 nm to 440 nm at which the absorption coefficient of hemoglobin is high.

If the intensity peak in the blue region of the CCD of the imaging section 11 is closer to the long-wavelength side than 440 nm, the peak wavelength of the blue laser light should exist the absorption peak of hemoglobin between 415 nm and 440 nm. This is preferable because a bright image with high contrast of the blood vessel K is easily obtained.

The fluorescent material included in the first fluorescent substance 7 is not limited to the silicate fluorescent material (EU-activated oxide fluorescent material), and may be a fluorescent material which absorbs light at a wavelength of 400 nm to 440 and which emits yellow broad fluorescence. It is also possible to use an EU-activated oxynitride fluorescent material or an EU-activated sulfide fluorescent material.

An oxide fluorescent material (YAG, TAG) having a Ce (cerium)-activated garnet crystal structure may be used as the fluorescent material included in the first fluorescent substance 7. The Ce-activated garnet-based fluorescent material is a material that can absorb light at a wavelength of 430 nm to 470 nm and emit yellow fluorescence, and can therefore be used in combination with the blue laser light having a peak at a wavelength of, for example, 430 nm to 440 nm. A light source which emits laser light having the peak wavelength of the first light emission spectrum in a wavelength region of 415 nm to 440 nm may be used as the excitation light source 3 which excites the first fluorescent substance 7.

If the light intensity at a wavelength of 450 nm to 480 nm in the blue region in the observation light P is less than or equal to ⅕ of the light intensity at a wavelength of 400 nm to 440 nm, fewer blue light components are received in the G pixels, and the influence as a noise component of the special light image is smaller. Preferably, the light intensity is less than or equal to 1/10.

A modification is described below.

Figure 7:
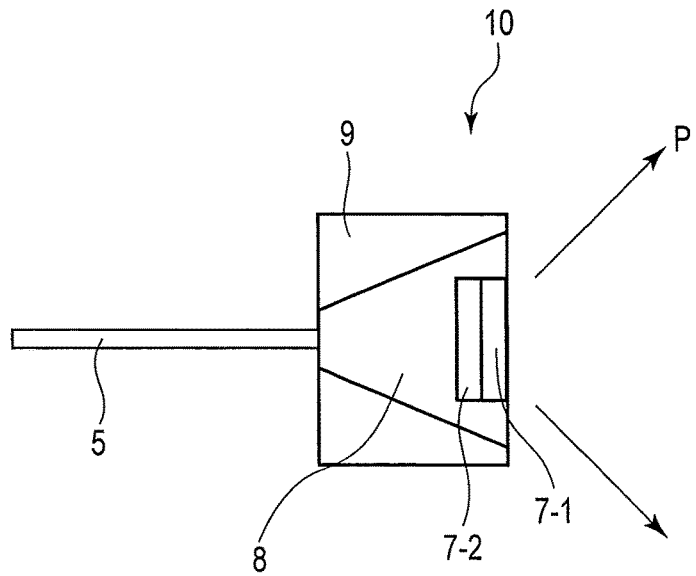
FIG. 7 is a schematically side view showing a modification of a wavelength converting unit in the system.

FIG. 7 shows a schematically side view of the wavelength converting unit 10. The wavelength converting unit 10 emits fluorescence at two wavelengths. The wavelength converting unit 10 has a second fluorescent substance 7-2 in addition to a first fluorescent substance 7-1, and the first fluorescent substance 7-1 and the second fluorescent substance 7-2 are stacked. The second fluorescent substance 7-2 absorbs the first light emission spectrum or the second light emission spectrum, and emits a third light emission spectrum having a peak wavelength closer to the long-wavelength side than the peak wavelength of the second light emission spectrum.

The component ratio between the first light emission spectrum, the second light emission spectrum and the third light emission spectrum is set so that the first light emission spectrum, the second light emission spectrum and the third light emission spectrum are mixed at a predetermined ratio and emitted substantially white light as the observation light P.

Specifically, the first fluorescent substance 7-1 absorbs light having a wavelength of 420 nm and then emits fluorescence in the green region, and includes an EU-activated oxynitride fluorescent material. FIG. 8 shows absorption/fluorescence characteristics of the first fluorescent substance 7-1.

The second fluorescent substance 7-2 emits fluorescence in the red region, and includes an EU-activated oxynitride fluorescent material. FIG. 9 shows absorption/fluorescence characteristics of the second fluorescent substance 7-2. The second fluorescent substance 7-2 may be a fluorescent material which absorbs and emits green fluorescence without absorbing a wavelength of 420 nm.

The wavelength converting unit 10 emits the observation light P that is white light in which the blue laser light having a wavelength of 420 nm, the green fluorescence and red fluorescence are mixed at a predetermined ratio.

According to the wavelength converting unit 10, the observation light P includes the white light having a flat spectrum from the green region to the red region, and color rendering properties during the normal light observation are improved. The wavelength converting unit 10 has the spectral component in the red region existing to the long-wavelength side compared to the above-mentioned first embodiment, so that how a large number of red tissues existing in the living tissue J inside the subject Q appear can be realized with high reproducibility.

[Second Embodiment]

Next, a second embodiment according to the present invention will be described with reference to the drawings.

Figure 10:
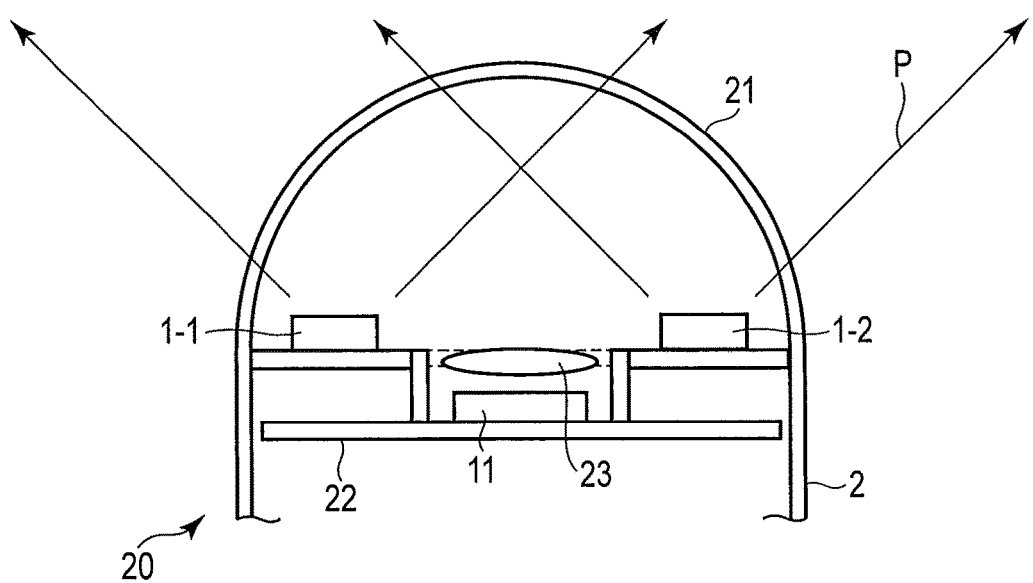
FIG. 10 is a schematically side view showing a capsule-type endoscope to which a second embodiment of a subject observation system according to the present invention is applied.

FIG. 10 shows a schematically side view showing a capsule-type endoscope 20 to which the subject observation system 100 according to the present invention is applied. The subject observation system 100 has a plurality of subject observation light sources, for example, six subject observation light sources 1-1, 1-2 and others mounted on the capsule-type endoscope 20. In FIG. 10, only two subject observation light sources 1-1 and 1-2 are shown to simplify the illustration.

The subject observation system 100 comprises the imaging section 11 which is introduced in the subject Q and which obtains image information about the inside of the subject Q. As in the above-mentioned configuration shown in FIG. 1, the subject observation system 100 comprises the capsule-type endoscope 20 which transmits the image information obtained by the imaging section 11 to the outside of the subject Q, the image processing section 12 which is disposed outside the subject Q and which receives the image information from the capsule-type endoscope 20 and then generates different images of the inside of the subject Q such as a normal light observation image and a special light observation image, and the image output section 13 which displays the normal light observation image and the special light observation image generated by the image processing section 12.

The capsule-type endoscope 20 comprises two subject observation light sources 1-1 and 1-2 which emit the observation light P to be applied to the inside of the subject Q, and an imaging element (imaging section) 10 which receives the reflected light F of the observation light P applied to the inside of the subject Q.

The capsule-type endoscope 20 includes semispherical housing 21 made of a light transmitting material. A ring-shaped substrate 22 having a cavity in the center is provided in the housing 21. On the substrate 22, for example, six subject observation light sources are provided as the subject observation light sources 1-1, 1-2 and the like as described above. On the substrate 22, a lens 23 is provided which collects the reflected light F from the subject Q to the imaging element 10. The imaging element 10 and the lens 23 are coaxially aligned.

Figure 11:
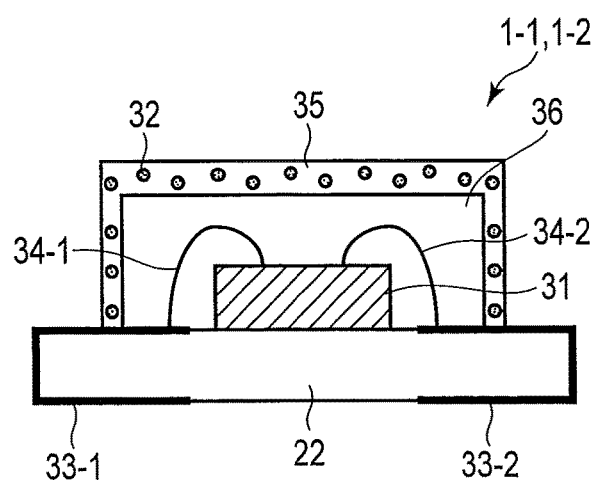
FIG. 11 is a schematically side view showing a subject observation light source in the system.

FIG. 11 shows a schematically side view of the subject observation light sources 1-1 and 1-2 and the like. Each of the subject observation light sources 1-1 and 1-2 comprises the substrate 22, a blue LED 31 as an excitation light source mounted on the substrate 22, and a fluorescent substance 32 provided to cover the blue LED 31. Electrodes 33-1 and 33-2 are respectively provided at both ends of the substrate 22. Each of the electrodes 33-1 and 33-2 is connected to an unshown battery, and is also electrically connected to the blue LED 31 via each of wire 34-1 and 34-2. Therefore, the blue LED 31 performs a light emitting operation when supplied with electric power from the unshown battery.

On the substrate 22, a first resin 35 is provided to cover the blue LED 31. The first resin 35 comprises light transmitting resin. The space between the first resin 35 and the blue LED 31 is filled with a second resin 36. The second resin 36 includes light transmitting resin.

The blue LED 31 has a peak at a wavelength of 420 nm, and emits blue LED light (the excitation light H) having a half-value width of about 20 nm.

The fluorescent substance 32 is, for example, a silicate powdered fluorescent material, and is enclosed in the first resin 35. The fluorescent substance 32 may be enclosed in the second resin 36 on the LED element.

Figure 12:
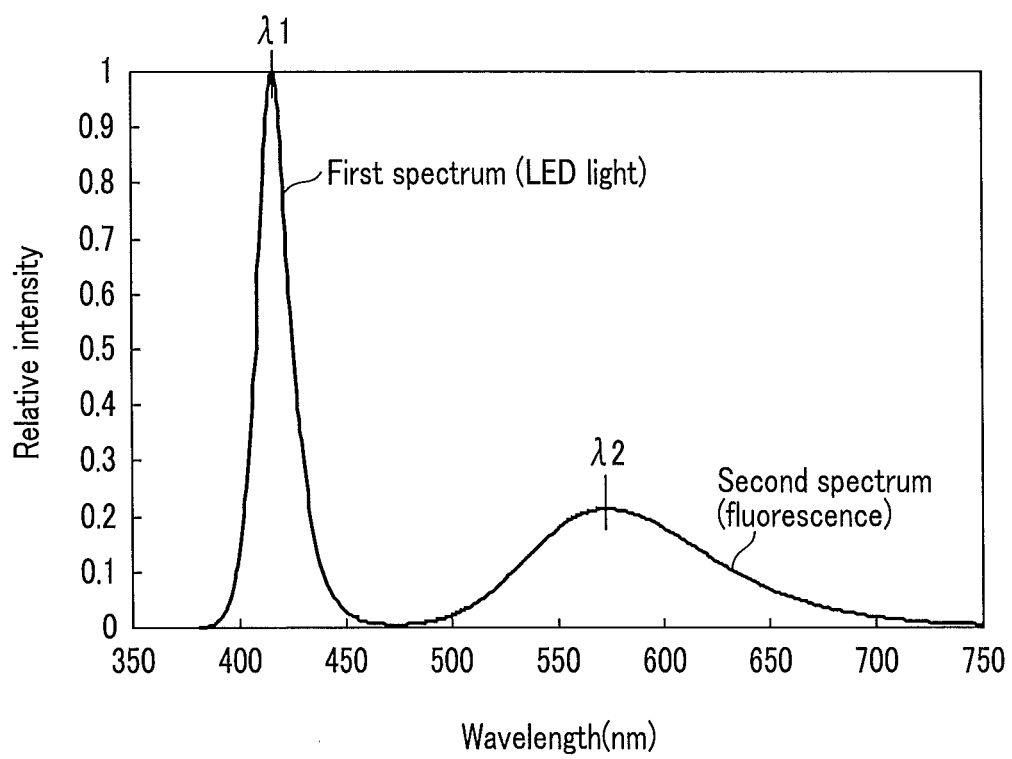
FIG. 12 is a graph showing spectral shape of observation light emitted from the subject observation light sources in the system.

FIG. 12 shows spectral shape of the observation light P emitted from the subject observation light sources 1-1 and 1-2 and the like. The observation light P emitted from the subject observation light sources 1-1 and 1-2 includes a peak at a wavelength of 420 nm, and emit white light based on the ratio between the blue LED light and yellow fluorescence. The light intensity in a wavelength region of 450 nm to 480 nm is less than or equal to one tenth of the light intensity in a wavelength region of 400 nm to 440 nm.

Next, the operation of the system having the above configuration is described. The operation similar to that in the above first embodiment is roughly described.

When supplied with electric power from the battery and performing a light emitting operation, the blue LED 31 emits blue LED light (excitation light H) having a peak at a wavelength of 420 nm and having a half-value width of about 20 nm. The blue LED light is applied to the fluorescent substance 32 enclosed in the first resin 35 through the second resin 36.

The fluorescent substance 32 absorbs part of the blue LED light emitted from the blue LED 31, and wavelength-converts the part of the blue LED light to fluorescence in the yellow region included in the green region, and also superimposes the blue LED light and the fluorescence in the yellow region and then emits the result as the white observation light P. The observation light P includes a peak at a wavelength of 420 nm as described above, and is emitted as white light due to the ratio between the blue LED light and the yellow fluorescence. The light intensity in a wavelength region of 450 nm to 480 nm is less than or equal to one tenth of the light intensity in a wavelength region of 400 nm to 440 nm.

Part of the observation light P is absorbed on the basis of the absorption characteristic of the blood vessel K and the living tissue J located in the irradiation region S. Part of the rest of the observation light P is scattered, reflected, and received by the CCD of the imaging section 11 having the R pixels, the G pixels and the B pixels.

The imaging section 11 outputs light reception signals of the RGB pixels received by the CCD. The light reception signals of the RGB pixels are transferred to the image processing section 12.

The first image generating section 12-1 of the image processing section 12 generates a normal light observation image on the basis of the levels of the pixel signals of the B pixels, the G pixels and the R pixels output from the CCD of the imaging section 11. That is, the first image generating section 12-1 generates the normal light observation image under observation light irradiation on the basis of the light reception signals of the B pixels, the G pixels and the R pixels, and predetermined image processing (e.g., white balance, noise reduction, structure enhancement, and gamma correction). The normal light observation image is generated by using all spectral components included in the observation light P.

The second image generating section 12-2 generates a special light observation image on the basis of the levels of the pixel signals of the B pixels and the G pixels output from the CCD of the imaging section 11. That is, the second image generating section 12-2 generates the special light observation image under observation light irradiation on the basis of signal processing that allocates the light reception signal of the B pixels as the light reception signals of the B pixels and the G pixels and allocates the light reception signal of the G pixels as the light reception signal of the R pixels, and on the basis of predetermined image processing. The special light observation image is generated by only using the blue region and the green region among the components included in the observation light.

The image output section 13 outputs the normal light observation image and the special light observation image generated in the image processing section 12 to, for example, the CRT display or the liquid crystal display.

Thus, according to the second embodiment described above, in the capsule-type endoscope 20, the observation lights P are emitted from the subject observation light sources 1-1 and 1-2 and the like equipped with the blue LED 31, scattered light and reflected light from the irradiation region S of the subject Q are received by the imaging section 11 and their light reception signals are output, the normal light observation image is generated by the first image generating section 12-1 on the basis of the levels of the pixel signals of the BGR pixels, and the special light observation image is generated by the second image generating section 12-2 on the basis of the levels of the pixel signals of the BG pixels. Therefore, it is possible to provide advantageous effects similar to the advantageous effects according to the first embodiment. Both the normal light observation and the special light observation can be used by one kind of observation light source combining the blue LED having a wavelength of 420 nm and the yellow fluorescence. It is not necessary to dispose multiple LEDs for multiple observations, which permits a size reduction.

Since the LED is used for the excitation light source 3, the observation light P can be emitted by an LED driving current having a low current consumption of several mA.

Therefore, the present embodiment is advantageously applied to an apparatus such as the capsule-type endoscope 20 having a small structure which is driven by the battery to emit the observation light P.

The inventions are not limited to the foregoing embodiments and various changes and modifications of its components may be made without departing from the scope of the present invention. Also, the components disclosed in the embodiments may be assembled in any combination for embodying the present invention. For example, some of the components may be omitted from all the components disclosed in the embodiments. Further, components in different embodiments may be appropriately combined.

What is claimed is:

1. A subject observation system comprising:
    a subject observation light source configured to emit observation light to a subject comprising a special observation target, wherein the observation light has a light emission spectrum comprising a first peak in a blue region, and a second peak in a green region and a red region; and
    a processor comprising hardware, wherein the processor is configured to:
        control an image sensor to generate an observation signal based on reflected light from the subject to which the observation light has been applied, wherein the observation signal has a blue signal based on a blue region of the reflected light, a green signal based on a green region of the reflected light, and a red signal based on a red region of the reflected light;
        generate a normal image comprising:
            a first normal pixel corresponding to the blue signal;
            a second normal pixel corresponding to the green signal; and
            a third normal pixel corresponding to the red signal; and
        generate a special image comprising:
            a first special pixel corresponding to one of the blue signal and the green signal;
            a second special pixel corresponding to the one of the blue signal and the green signal; and
            a third special pixel corresponding to the other of the blue signal and the green signal,
        wherein the first to third normal pixels and the first to third special pixels represent the same portion of the subject.

2. The subject observation system according to claim 1, wherein the subject observation light source comprises:
    an excitation light source configured to emit excitation light; and a wavelength converter configured to wavelength convert the excitation light emitted from the excitation light source, and then emit the observation light comprising the excitation light.

3. The subject observation system according to claim 2, wherein the excitation light has a light emission spectrum comprising the first peak in the blue region, and
wherein the wavelength converter comprises a fluorescent substance configured to:
   transmit a first part of the excitation light; and
   wavelength-convert a second part of the excitation light to fluorescence including a predetermined emission spectrum and emit the fluorescence.

4. The subject observation system according to claim 1, wherein the processor is configured to generate the normal image and the special image such that a contrast of the special observation target in the special image is higher than a contrast of the special observation target in the normal image.

5. The subject observation system according to claim 1, wherein the image sensor comprises:
   a blue pixel configured to generate the blue signal;
   a green pixel configured to generate the green signal; and
   a red pixel configured to generate the red signal, and
wherein the processor is configured to generate the normal image and the special image of the same portion of the subject, on the basis of the blue signal, the green signal and the red signal, in parallel in one frame period.

6. The subject observation system according to claim 1, wherein a peak wavelength of a light emission spectrum in the blue region exists in a wavelength region having an absorption coefficient equal to or more than one fifth of a value of the absorption coefficient of the absorption peak wavelength at which the absorption coefficient of the special observation target in a visible light range is maximized, and
wherein a maximum intensity of the light emission spectrum in the blue region is higher than the maximum intensities of each of the light emission spectra in the green region and the red region.

7. The subject observation system according to claim 6, wherein the peak wavelength of the light emission spectrum in the green region exists in a wavelength region having an absorption coefficient equal to or more than half of the value of the absorption coefficient at the absorption peak wavelength at which the absorption coefficient of the special observation target in a wavelength region of 525 nm to 555 nm included in the green region is maximized.

8. The subject observation system according to claim 2, wherein the excitation light emitted by the excitation light source has a first light emission spectrum including the wavelength of a light emission peak in a wavelength region of 400 nm to 440 nm included in the blue region,
wherein the wavelength converter is configured to absorb part of the excitation light having the first light emission spectrum, and also convert the part of the excitation light having the first light emission spectrum to a converted light having a second light emission spectrum including a wavelength region of 525 nm to 555 nm included in the green region, and then emit the observation light which contains superposition of the first light emission spectrum and the second light emission spectrum,
wherein a light intensity of the observation light in a wavelength region of 450 nm to 480 nm included in the blue region is one fifth of a light intensity of the observation light in a wavelength region of 400 nm to 440 nm, and
wherein a light intensity of the observation light in a wavelength region of 600 nm or more included in the red region is equal to or more than one third of a light intensity of the observation light in a wavelength region of 525 nm to 555 nm.

9. The subject observation system according to claim 2, wherein the excitation light emitted by the excitation light source has a first light emission spectrum including a wavelength of a light emission peak in a wavelength region of 400 nm to 440 nm included in the blue region,
wherein the wavelength converter is configured to absorb part of the excitation light having the first light emission spectrum, and also convert the absorbed part of the excitation light to a converted light having a second light emission spectrum including a wavelength region of 525 nm to 555 nm included in the green region, and then emit the observation light which contains superposition of the first light emission spectrum and the second light emission spectrum,
wherein the second light emission spectrum includes a continuous light emission spectral component in a wavelength region of 525 nm to 600 nm included in the green region to the red region, and
wherein a minimum intensity of the converted light in the wavelength region of 525 nm to 600 nm is equal to or more than one fifth of the peak intensity of the second light emission spectrum.

10. The subject observation system according to claim 8, wherein the excitation light source comprises a laser diode configured to emit the excitation light, wherein the excitation light has the first light emission spectrum,
wherein the wavelength converter comprises a first fluorescent substance configured to absorb the part of the excitation light having the first light emission spectrum emitted from the laser diode, and emit a converted light having the second light emission spectrum having a peak wavelength at a wavelength of 525 nm or more, and
wherein the subject observation light source further comprises a light guide member configured to guide the excitation light having the first light emission spectrum emitted from the laser diode, and apply the excitation light having the first light emission spectrum that is guided to the first fluorescent substance.

11. The subject observation system according to claim 8, wherein the observation light is configured so that the wavelength region having an intensity that is less than or equal to 1/20 of the peak intensity of the first light emission spectrum continuously exists 5 nm or more in a wavelength region of 450 nm to 480 nm.

12. The subject observation system according to claim 10, wherein the excitation light source is configured so that the peak wavelength of the first light emission spectrum exists in a wavelength region between the wavelength at which the absorption spectrum of the first fluorescent substance in a wavelength region of 400 nm to 440 nm is maximized and the peak wavelength of the absorption of the special observation target in the wavelength region of 400 nm to 440 nm.

13. The subject observation system according to claim 10, wherein the first fluorescent substance includes a Ce-activated garnet-based fluorescent material, and
wherein the excitation light emitted by the excitation light source includes the peak wavelength of the first light emission spectrum in a wavelength region of 415 nm to 440 nm.

14. The subject observation system according to claim 10, wherein a component ratio between the first light emission spectrum and the second light emission spectrum is set so that the wavelength converter mixes the excitation light having the first light emission spectrum and the converted light having the second light emission spectrum at a predetermined ratio to emit substantially white light as the observation light.

15. The subject observation system according to claim 10, wherein the wavelength converter further comprises a second fluorescent substance configured to:
    absorb the part of the excitation light having the first light emission spectrum or the converted light having the second light emission spectrum; and
    emit an emitted light having a third light emission spectrum including a peak wavelength closer to a long-wavelength side than the peak wavelength of the converted light having the second light emission spectrum.

16. The subject observation system according to claim 15, wherein the component ratio between the first light emission spectrum, the second light emission spectrum, and the third light emission spectrum is set so that the excitation light having first light emission spectrum, the converted light having the second light emission spectrum, and the emitted light having the third light emission spectrum are mixed at a predetermined ratio to emit substantially white light as the observation light.

17. The subject observation system according to claim 8, wherein the image sensor comprises blue pixels, green pixels and red pixels which respectively have maximum sensitivities in three regions: the blue region, the green region and the red region, and
wherein the first light emission spectrum exists in the blue region.

18. The subject observation system according to claim 8, wherein the excitation light emitted by the excitation light source includes the peak wavelength of the first light emission spectrum in a wavelength region between an absorption peak wavelength of the special observation target at a wavelength of 400 nm to 440 nm and the peak wavelength of the light receiving sensitivity of a blue pixel in the image sensor.

19. A capsule-type endoscope system comprising:
a capsule casing; and
the subject observation system according to claim 1, wherein the subject observation system is arranged to the capsule casing.

20. The subject observation system according to claim 3, wherein the predetermined emission spectrum is in a yellow region, and
wherein a mixture of the first part of the excitation light that is transmitted and the fluorescence in a predetermined ratio renders the light emission spectrum of the observation light substantially white.

21. The subject observation system according to claim 1, wherein the special observation target is hemoglobin.

22. A subject observation method comprising:
controlling a subject observation light source to emit observation light to a subject comprising a special observation target, wherein the observation light has a light emission spectrum comprising a first peak in a blue region, and a second peak in a green region and a red region;
controlling an image sensor to generate an observational signal based on reflected light from the subject to which the observation light has been applied, wherein the observation signal has a blue signal based on a blue region of the reflected light, a green signal based on a green region of the reflected light, and a red signal based on a red region of the reflected light;
generating a normal image comprising:
    a first normal pixel corresponding to the blue signal;
    a second normal pixel corresponding to the green signal; and
    a third normal pixel corresponding to the red signal; and
generating a special image comprising:
    a first special pixel corresponding to one of the blue signal and the green signal;
    a second special pixel corresponding to the one of the blue signal and the green signal; and
    a third special pixel corresponding to the other of the blue signal and the green signal,
    wherein the first to third normal pixels and the first to third special pixels represent the same portion of the subject.

* * * * *